(12) United States Patent
Cho et al.

(10) Patent No.: US 9,802,910 B2
(45) Date of Patent: Oct. 31, 2017

(54) METHOD FOR PREPARING 5-HYDROXYMETHYL-2-FURFURAL USING ACID CATALYST IN PRESENCE OF ETHYLENE GLYCOL-BASED COMPOUND SOLVENT DERIVED FROM BIOMASS

(71) Applicant: KOREA INSTITUTE OF INDUSTRIAL TECHNOLOGY, Cheonan-Si, Chungcheongnam-Do (KR)

(72) Inventors: Jin Ku Cho, Yongin-Si (KR); Sang Yong Kim, Cheonan-Si (KR); Bo Ra Kim, Daejeon (KR); Seung Han Shin, Seoul (KR)

(73) Assignee: KOREA INSTITUTE OF INDUSTRIAL TECHNOLOGY, Cheonan (KR)

( * ) Notice: Subject to any disclaimer, the term of this patent is extended or adjusted under 35 U.S.C. 154(b) by 0 days.

(21) Appl. No.: 14/915,192

(22) PCT Filed: Aug. 28, 2014

(86) PCT No.: PCT/KR2014/008034
§ 371 (c)(1),
(2) Date: Feb. 26, 2016

(87) PCT Pub. No.: WO2015/030505
PCT Pub. Date: Mar. 5, 2015

(65) Prior Publication Data
US 2016/0207896 A1 Jul. 21, 2016

(30) Foreign Application Priority Data
Aug. 29, 2013 (KR) .................. 10-2013-0103028

(51) Int. Cl.
C07D 307/50 (2006.01)
C07D 307/46 (2006.01)

(52) U.S. Cl.
CPC ................... C07D 307/46 (2013.01)

(58) Field of Classification Search
USPC ................................. 549/489, 488
See application file for complete search history.

(56) References Cited

U.S. PATENT DOCUMENTS

2009/0030215 A1   1/2009  Dignan et al.

FOREIGN PATENT DOCUMENTS

| CN | 102603532 | | 7/2012 | |
|---|---|---|---|---|
| GB | 876463 | * | 9/1961 | ........... C07D 307/46 |
| JP | 2009-057345 A | | 3/2009 | |
| KR | 10-2010-0121736 A | | 11/2010 | |
| KR | 10-2011-0079484 A | | 7/2011 | |
| KR | 1020120121323 | | 11/2012 | |
| KR | 1020130000147 | | 1/2013 | |
| WO | WO2006-063220 A2 | | 6/2006 | |

OTHER PUBLICATIONS

Jeong, J. et al.: Commercially attractive process for production of 5-hydroxymethyl-2-furfural from high fructose corn syrup. J. of Industrial & Engin. Chem. , vol. 19, pp. 1106-1111, 2013.*
Aellig, C. et al.: Continuous D-Fructose dehydration to 5-hydroxymethylfurfural under mild conditions. Chemsuschem, vol. 5, pp. 1737-1742, 2012.*
G. Sampath et al., "Fructose dehydration to 5-hydroxymethylfurfural: Remarkable aolvent influence on recyclability of Amberlyst-15 catalyst and regeneration stidies", Catalysis Communications, Mar. 27, 2013, vol. 37, pp. 41-44.
Jaewon Jeong et al., Commerciaiiy attractive process for production of 5-hydroxymethyl-2-furfural from high fructose corn syrup, Journal of Industrial and Engineering Chemistry 19 (2013) 1106-1111.

* cited by examiner

Primary Examiner — Charanjit Aulakh
(74) Attorney, Agent, or Firm — STIP Law Group, LLC

(57) ABSTRACT

Provided is a method for preparing 5-hydroxymethyl-2-furfural using an acid catalyst in the presence of an ethylene glycol-based solvent. The method for preparing the 5-hydroxymethyl-2-furfural involves using a linear or cyclic ethylene glycol-based compound as a solvent and producing the 5-hydroxymethyl-2-furfural from fructose, in the presence of the acid catalyst, thereby reducing the dependency on petroleum in response to greenhouse gas emission regulations. Also, a high yield of the 5-hydroxymethyl-2-furfural can be obtained from fructose, and the solvent and the catalyst can be efficiently separated, collected, and reused after a reaction has completed.

10 Claims, 2 Drawing Sheets

METHOD FOR PREPARING 5-HYDROXYMETHYL-2-FURFURAL USING ACID CATALYST IN PRESENCE OF ETHYLENE GLYCOL-BASED COMPOUND SOLVENT DERIVED FROM BIOMASS

This is a U.S. national stage application of PCT Application No. PCT/KR2014/008034 under 35 U.S.C. 371, filed Aug. 28, 2014 in Korean, claiming the priority benefit of Korean Application No. 10-2013-0103028, filed Aug. 29, 2013, which is hereby incorporated by reference.

TECHNICAL FIELD

The present disclosure relates to the preparation of 5-hydroxymethyl-2-furfural. More particularly, the present disclosure relates to a method for preparing 5-hydroxymethyl-2-furfural, a platform compound for high value-added biofuels or biochemicals, from fructose using a biomass-derived ethylene glycol-based solvent and an acid catalyst.

BACKGROUND ART

Because of their finite reserves, global petroleum resources are running out. With many developing countries currently industrializing, petroleum demand has sharply increased, causing an imbalance between market demand and supply and leading to an era of high oil prices. Furthermore, the reckless use of petroleum has brought about an explosive increase in greenhouse gases, provoking significant environmental problems such as global warming.

Extensive worldwide efforts have long been made to use biomass, which is regenerable and sustainable, as an alternative to petroleum resources. As a result, biofuels, such as bioethanol, biodiesel, etc. and bioplastic monomers, such as lactic acid, propanediol, etc., are successfully produced on an industrial scale and are used as substitutes for transportation fuels or petrochemical materials.

In recent years, intensive attention has been paid to 5-hydroxymethyl-2-furfural (HMF), a furan compound, as it has been discovered to be producible via conversion of biomass-derived carbohydrates.

Through oxidation, HMF can be converted into 2,5-furan dicarboxylic acid (FDCA), a known alternative to terephthalic acid (TPA). TPA is a monomer of poly(ethylene terephthalate) (PET). PET, which is used in a wide spectrum of fields including food and beverage containers, is synthesized through polycondensation between the monomers ethylene glycol (EG) and terephthalic acid (TPA). For the synthesis of biomass-based PET, its monomers EG and TPA should be derived from biomass. Currently, EG is industrially produced from bioethanol-based bioethylene. As for TPA, its synthesis based on biomass has not yet been achieved.

Recently, HMF has aroused keen interest for its use as a core intermediate for bioplastics and biofuels. Extensive studies have been directed toward the mass production of HMF, but none have yet succeeded in developing processes for the industrial mass production of HMF.

DMSO (dimethyl sulfoxide) is known as the most effective solvent for use in the conversion of fructose into HMF. HMF can be produced at excellent yield when fructose is heated for 1~2 hrs at 80~150° C. under an acidic condition in DMSO. However, the direct extraction of HMF from the DMSO solvent is difficult not only because DMSO is difficult to remove by distillation due to its high boiling point of 189° C., but also because DMSO is miscible with most solvents.

To avoid such problems, a strategy was suggested in which the conversion is conducted in a bicomponent system consisting of DMSO and a different solvent, with the real-time extraction of HMF from the solvent system (G. W. Huber, J. N. Chheda, C. J. Barrett, J. A. Dumesic, Science 2005, 308, 1446). However, only a limited amount of HMF can be extracted from the solvent system, and the solvent cannot be reused.

In place of DMSO, alternatives have been employed, such as DMF for its lower boiling point (G. A. Halliday, R. J. Young, V. V. Grushin, Org. Lett. 2003, 5, 2003) and ionic liquid for easy extraction of the product (H. B. Zhao, J. E. Holladay, H. Brown, Z. C. Zhang, Science, 2007, 316, 1597). However, DMF still has a high boiling point (153° C.) and ionic liquid is economically unfavorable for use in industrial mass production due to its high price.

Industrially, fructose is obtained from glucose through a catalytic process, and is marketed as a syrup containing about 20~30 wt % of water. The direct use of a fructose in syrup form for HMF conversion is expected to reduce the cost of drying fructose into powder.

DISCLOSURE

Technical Problem

Accordingly, the present disclosure has been made keeping in mind the above problems occurring in the prior art, and an object of the present disclosure is to provides a method for preparing 5-hydroxymethyl-2-furfural in which a biomass-derived non-petroleum solvent is employed, whereby dependence of the chemical industry on petroleum can be alleviated and the regulation of greenhouse gases can be achieved, at least in part.

Also, the present disclosure provides a method for preparing 5-hydroxymethyl-2-furfural from fructose at high yield whereby the solvent and the catalyst can be effectively separated from each other after the completion of the reaction, and thus can be reused.

Technical Solution

In order to accomplish the above object, the present disclosure provides a method for preparing 5-hydroxymethyl-2-furfural, comprising converting fructose into 5-hydroxymethyl-2-furfural in the presence of an acid catalyst in a linear or cyclic ethylene glycol-based compound as a solvent.

In some embodiments of the present disclosure, the linear ethylene glycol-based compound may be represented by the following Structural Formula:

[Structural Formula 1]

$$R^1-O\underbrace{\phantom{xxx}\diagdown\diagup\phantom{xxx}O}_{m}-R^2$$

wherein, $R^1$ and $R^2$ may be the same or different and are each independently C1 to C6 alkyl, and m is an integer of 1 to 6.

In some embodiments, $R^1$ and $R^2$ may be the same or different and are each independently methyl or ethyl, and m is an integer of 1 to 4.

In some embodiments, the cyclic ethylene glycol-based compound may be a compound represented by the following Structural Formula 2:

[Structural Formula 2]

wherein,
n is an integer of 1 to 6.

In particular embodiments, n may be an integer of 1 to 3.

In some embodiments, the linear or cyclic ethylene glycol-based compound may be derived from ethanol, the ethanol being prepared from biomass by fermentation.

In some embodiments, the linear or cyclic ethylene glycol-based compound may be selected from a group consisting of 1,4-dioxane, monoethylene glycol dimethyl ether, diethylene glycol dimethyl ether, triethylene glycol dimethyl ether, tetraethylene glycol dimethyl ether, and combinations thereof.

In some embodiments, the fructose may be provided as a fructose syrup having a water content of 10 to 50 weight parts per 100 weight parts of fructose.

In some embodiments, the acid catalyst may comprise at least one selected from the group consisting of an inorganic acid catalyst, an organic acid catalyst, and a solid acid catalyst.

In some embodiments, the inorganic acid catalyst may be at least one selected from the group consisting of sulfuric acid, nitric acid, and phosphoric acid.

In some embodiments, the organic acid catalyst may be at least one selected from the group consisting of C1 to C6 alkylsulfonic acid, C6 to C14 arylsulfonic acid, C7 to C20 alkylarylsulfonic acid, and C7 to C20 arylalkylsulfonic acid.

In some embodiments, the solid acid catalyst may be structured to have an organic or inorganic support to which Brönsted acid or Lewis acid is linked as a functional group.

In some embodiments, the organic support may be at least one selected from the group consisting of polystyrene, polyamide, and polyethylene glycol.

In some embodiments, the inorganic support may comprise at least one selected from among silica, alumina, and zeolite.

In some embodiments, the solid acid catalyst may contain amorphous carbon into which a sulfonic acid group has been introduced, the amorphous carbon being formed by incompletely carbonizing biomass.

In some embodiments, the converting is carried out at 80 to 150° C.

In some embodiments, the method may further comprise recovering the acid catalyst from the solvent after the converting step when the acid catalyst is a solid acid catalyst.

Advantageous Effects

Featuring the employment of a biomass-derived non-petroleum solvent, the method for preparing 5-hydroxymethyl-2-furfural in accordance with the present disclosure can alleviate dependence of the chemical industry on petroleum and achieve the regulation of greenhouse gases, at least in part. In addition, 5-hydroxymethyl-2-furfural can be produced from fructose at high yield using the method, and the solvent and the catalyst can be effectively separated from each other after completion of the reaction, and thus can be reused.

BEST MODE

Figure 1:
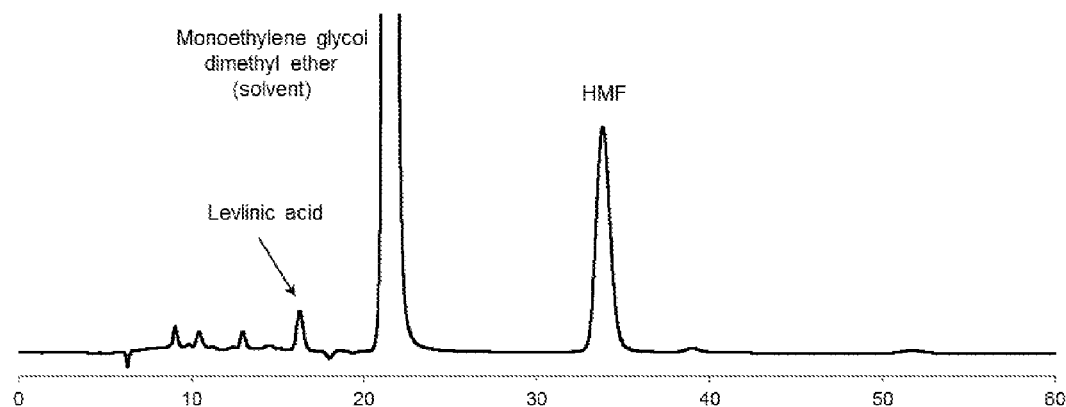
FIG. 1 is an HPLC chromatogram, read during the preparation of 5-hydroxymethyl-2-furfural as indicated in Example 1.

The embodiment of the present invention described hereinbelow is provided for allowing those skilled in the art to more clearly comprehend the present invention.

However, it should be understood that the exemplary embodiments according to the concept of the present invention are not limited to the embodiments which will be described hereinbelow with reference to the accompanying drawings, but various modifications, equivalents, additions and substitutions are possible, without departing from the scope and spirit of the invention. In the following description, it is to be noted that, when the functions of conventional elements and the detailed description of elements related with the present invention may make the gist of the present invention unclear, a detailed description of those elements will be omitted.

The terminology used herein is for the purpose of describing particular embodiments only and is not intended to limit the invention. As used herein, the singular forms "a", "an" and "the" are intended to include the plural forms as well, unless the context clearly indicates otherwise. It will be further understood that the terms "comprises" and/or "comprising," or "includes" and/or "including," when used in this specification, specify the presence of stated features, regions, integers, steps, operations, elements and/or components, but do not preclude the presence or addition of one or more other features, regions, integers, steps, operations, elements, components and/or groups thereof.

Below, embodiments of the present invention will be explained in detail. Therefore, the detailed description provided below should not be construed as being restrictive. In addition, the scope of the present invention is defined only by the accompanying claims and their equivalents if appropriate.

Unless defined otherwise, the term "alkyl", as used herein, refers to a linear, branched, or cyclic aliphatic hydrocarbon. The alkyl may be a "saturated alkyl" free of double and triple bonds.

The alkyl may be an "unsaturated alkyl" with at least one double or triple bond.

The alkyl may be a C1 to C6 alkyl, and particularly a C1 to C3 alkyl.

For example, a C1 to C4 alkyl means an alkyl chain of 1 to 4 carbon atoms, such as methyl, ethyl, propyl, iso-propyl, n-butyl, iso-butyl, sec-butyl, and t-butyl.

Examples of the alkyl useful in the present disclosure include methyl, ethyl, propyl, isopropyl, butyl, isobutyl, t-butyl, pentyl, hexyl, ethenyl, propenyl, butenyl, cyclopropyl, cyclobutyl, cyclopentyl, and cyclohexyl.

In the method for preparing 5-hydroxymethyl-2-furfural (HMF), fructose is dehydrated in the presence of an acid catalyst in a linear or cyclic ethylene glycol-based compound solvent to give HMF.

The preparation mechanism of 5-hydroxymethyl-2-furfural from fructose by dehydration is as illustrated in the following Reaction Scheme 1.

production yield of 5-hydroxymethyl-2-furfural may decrease and the solvent may be difficult to separate after completion of the reaction, making it impossible to recycle.

In addition, larger alkyl radicals ($R^1$ and $R^2$) exhibit higher hydrophobicity and less compatibility with fructose, and thus may be prone to decreasing the yield of 5-hydroxymethyl-2-furfural.

[Reaction Scheme 1]

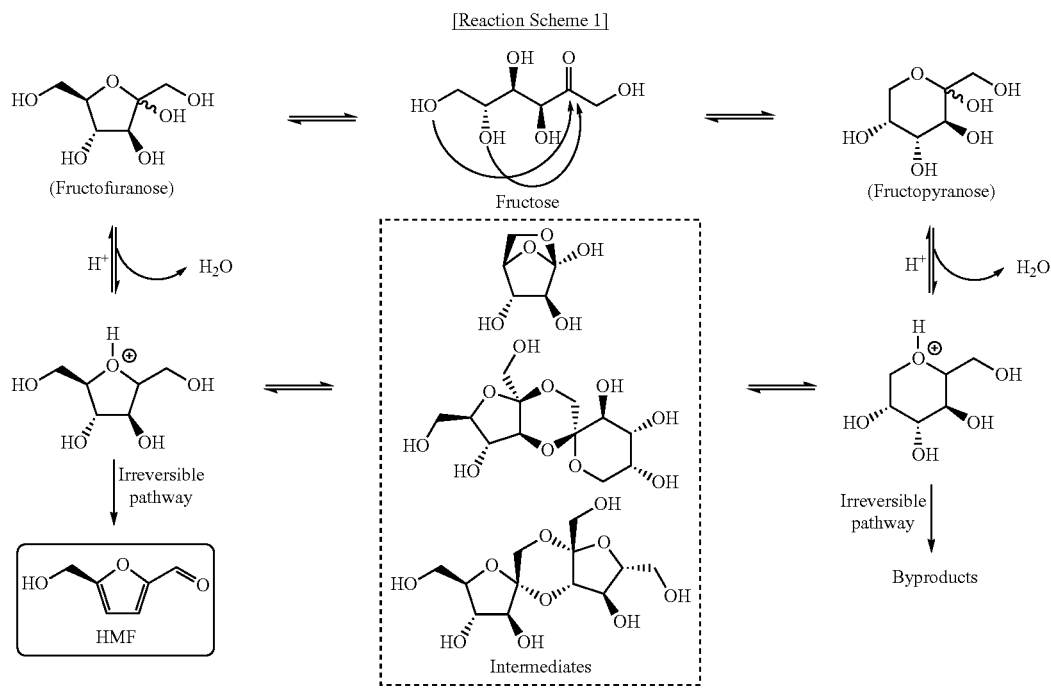

Acting as reversible fructose reservoirs during conversion from fructose into 5-hydroxymethyl-2-furfural, the intermediate compounds of Reaction Scheme 1 can block the reaction from entering the fructopyranose pathway, which leads to the production of undesired by-products such as humin.

The linear or cyclic ethylene glycol-based compound solvent is useful in stabilizing the intermediate compounds, thus contributing to the production of 5-hydroxymethyl-2-furfural from fructose at high yield.

The linear ethylene glycol-based compound usefully available as a solvent may be represented by the following Structural Formula 1.

[Structural Formula 1]

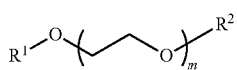

wherein,
$R^1$ and $R^2$, which may be the same or different, are each independently C1 to C6 alkyl, and
m is an integer of 1 to 6.

As can be seen in Structural Formula 1, the linear ethylene glycol-based compound solvent has a repeating ethylene glycol unit, with the terminal hydroxy protected in the form of alkyl ether.

The number of the repeating ethylene glycol unit (m) may be 1 to 6, and particularly 1 to 4. If m is higher than 6, the $R^1$ and $R^2$ may be the same or different, and are each independently a C1 to C6 alkyl. In some embodiments of the present disclosure, $R^1$ and $R^2$ may be the same or different, and are each independently methyl or ethyl.

Further, the cyclic ethylene glycol-based compound available as the solvent may be a compound represented by the following Structural Formula 2:

[Structural Formula 2]

wherein,
n is an integer of 1 to 6.

The cyclic ethylene glycol-based compound useful as the solvent may have a cyclic molecular structure consisting of a repeating unit of ethylene glycol, as shown in Structural Formula 2.

Particularly, the number of the repeating ethylene glycol unit (n) may be 1 to 6, and more particularly 1 to 3. If n is over 6, the compound is too chemically unstable in an acidic catalyst condition to serve as a solvent.

For use as a biomass-derived solvent, the linear or cyclic ethylene glycol-based compound may be prepared from the ethanol obtained by biomass fermentation. The mechanism for preparing the biomass-derived ethylene glycol-based compound is schematically illustrated in the following Reaction Scheme 2.

[Reaction Scheme 2]

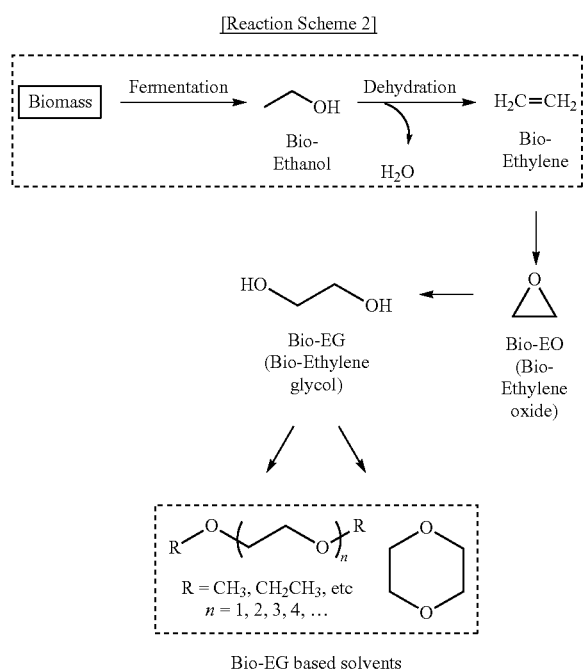

Bio-EG based solvents

Since it is derived from bio-ethanol, which is currently industrially produced, the ethylene glycol-based compound useful as a solvent in the present disclosure can be prepared at low cost and can decrease petroleum dependence.

Examples of the linear or cyclic biomass-derived ethylene glycol-based compound useful as a solvent include 1,4-dioxane, monoethylene glycol dimethyl ether, diethylene glycol dimethyl ether, triethylene glycol dimethyl ether, and tetraethylene glycol dimethyl ether.

As needed, the ethylene glycol-based compound solvent may be diluted in water.

The acid catalyst may be inorganic or organic. In consideration of ease of separation and reuse, a solid acid catalyst may be employed.

Representative among the inorganic catalyst are sulfuric acid, nitric acid, and phosphoric acid.

The organic acid catalyst may be a C1 to C6 alkylsulfonic acid, a C6 to C14 arylsulfonic acid, a C7 to C20 alkylarylsulfonic acid, or a C7 to C20 arylalkylsulfonic acid. Particularly, paratoluene sulfonic acid, methane sulfonic acid, alkanesulfonic acid, arylsulfonic acid, benzene sulfonic acid, or linear alkylbenzene sulfonic acid may be used.

As for the solid acid catalyst, its structure is based on an organic or inorganic support to which a Brönsted acid or Lewis acid is linked.

The organic support may be a polymer support comprising polystyrene, polyamide, polyethylene glycol, etc. The inorganic support may be based on silica, alumina, zeolite, etc.

As a catalytically active ingredient chemically linked to the support, the acid may be a Brönsted acid including sulfonic acid, phosphoric acid, etc., or a Lewis acid including a metal ion coordinated to a ligand.

Herein, the term "Brönsted acid" refers to a substance that donates a proton ($H^+$) in the context of an acid-base reaction, as defined by Brönsted-Lowry. The term "Lewis acid" means a substance that accepts an electron pair in an acid-base reaction, as defined by Lewis.

For use in the present disclosure, the solid acid catalyst may comprise a sulfuric acid that is introduced into an amorphous carbon support formed through incomplete carbonization of biomass.

The amorphous carbon can be obtained by incompletely carbonizing biomass. In some embodiments of the present disclosure, the biomass may be lignocellulosic biomass, examples of which include, but are not limited to, woods and rice straw. Particularly, the lignocellulosic biomass may contain lignin in an amount of 10 to 40 wt %.

The incomplete carbonization may be conducted chemically using a dehydrating agent or thermally. Thermal treatment for incomplete carbonization may be carried out at 400 to 600° C.

Subsequently, sulfuric acid comprising sulfur trioxide ($SO_3$) is added to the amorphous carbon to introduce sulfonic acid into the amorphous carbon. Particularly, the sulfuric acid contains sulfur trioxide in an amount of 15 to 50 wt %.

As prepared into an amorphous carbon form with sulfonic acid introduced thereinto, the solid acid catalyst may contain sulfonic acid in an amount of 0.4 to 0.8 mmol per gram of sulfonic acid.

For use in the present disclosure, the fructose is particularly in the form of a syrup containing water and fructose.

In this regard, the syrup particularly contains water in an amount of 10 to 50 weight parts based on 100 weight parts of fructose, and more particularly in an amount of 20 to 30 weight parts.

Because the ethylene glycol-based compound solvent used in the present disclosure is not completely miscible with water, fructose may not be used in the form of powder, but may be used in the form of having been mixed with water. Hence, an additional process of drying fructose is obviated.

The dehydration reaction may be particularly carried out at 80 to 150° C. At a reaction temperature of less than 80° C., the reaction rate may be slowed. On the other hand, a reaction temperature higher than 150° C. may increase the incidence of side reactions.

The reaction time may vary depending on the reaction temperature. A lower reaction temperature is associated with a longer reaction time. At a high reaction temperature, the reaction is conducted for a relatively short period of time. Briefly, the reaction time may be set to a range from 0.5 to 9 hrs at a reaction temperature of 120° C., particularly from 1 to 6 hrs, and more particularly from 2 to 4 hrs. The reaction may be relatively lengthened at temperatures lower than 120° C. and shortened at temperatures higher than 120° C.

With regard to reaction pressure, the reaction can be carried out at an atmospheric pressure when the reaction temperature is set to be less than the boiling point of a reaction solvent, which is convenient and economically beneficial. A reaction temperature higher than the boiling point of a reaction solvent requires a reaction apparatus that can endure the elevated pressure attributable to the vapor pressure of the solvent, but has the advantage of shortening the reaction time. Therefore, both the reaction pressure and the reaction temperature may be properly adjusted depending on the situation.

A better understanding of the present invention may be obtained through the following examples which are set forth to illustrate, but are not to be construed as limiting the present invention.

EXAMPLES

Example 1

In a 38 mL thick-glass-walled pressure tubular reactor (having an O.D. of 25.5 mm and a length of 20.3 cm) equipped with a Teflon screw cap, a fructose syrup (150 mmol, 25% water) was placed, together with the solid acid catalyst Amberlyst-15 (300 mg), followed by adding the EG-based solvent monoethylene glycol dimethyl ether (3 mL). The resulting solution was heated at 120° C. for 2 hrs while stirring at 700 rpm. After completion of the reaction, the reaction mixture was cooled to room temperature and diluted 100-fold in distilled water. HPLC and $^1$H NMR analyses were conducted, and the data are depicted in FIGS. 1 and 2, respectively.

Figure 2:
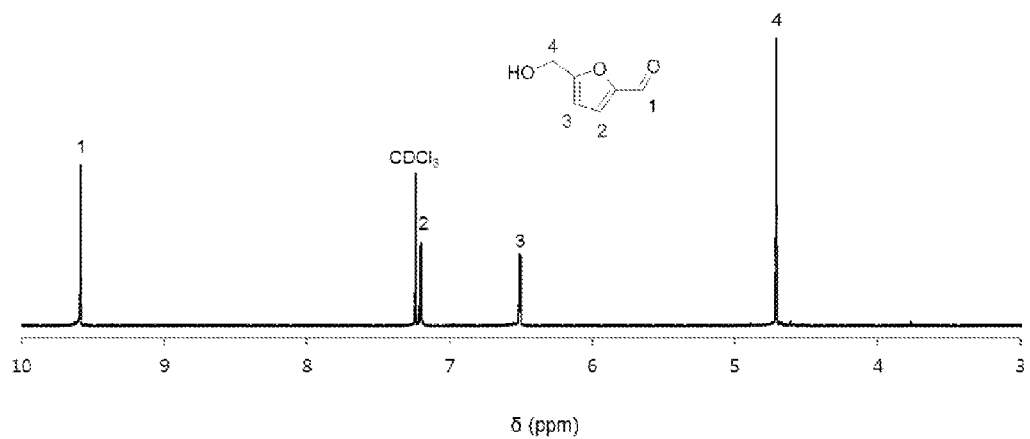
FIG. 2 is a $^1$H NMR profile of HMF, taken after the preparation of 5-hydroxymethyl-2-furfural as indicated in Example 1.

As can be seen in FIGS. 1 and 2, $^1$H NMR data identified the product as HMF while HPLC data indicated the production of HMF at a yield of 80%.

Example 2

In a 38 mL thick-glass-walled pressure tubular reactor (having an O.D. of 25.5 mm and a length of 20.3 cm) equipped with a Teflon screw cap, a fructose syrup (150 mmol, 25% water) was placed, together with the solid acid catalyst Amberlyst-15 (300 mg), followed by adding the EG-based solvent 1,4-dioxane (3 mL). The resulting solution was heated at 120° C. for 2 hrs while stirring at 700 rpm. After completion of the reaction, the reaction mixture was cooled to room temperature and diluted 100-fold in distilled water. HPLC analysis was conducted, indicating the production of HMF at a yield of 78%.

Example 3

In a 38 mL thick-glass-walled pressure tubular reactor (having an O.D. of 25.5 mm and a length of 20.3 cm) equipped with a Teflon screw cap, a fructose syrup (150 mmol, 25% water) was placed, together with the solid acid catalyst Amberlyst-15 (300 mg), followed by adding the EG-based solvent diethylene glycol dimethyl ether (3 mL). The resulting solution was heated at 120° C. for 2 hrs while stirring at 700 rpm. After completion of the reaction, the reaction mixture was cooled to room temperature and diluted 100-fold in distilled water. HPLC analysis was conducted, indicating the production of HMF at a yield of 79%.

Example 4

In a 38 mL thick-glass-walled pressure tubular reactor (having an O.D. of 25.5 mm and a length of 20.3 cm) equipped with a Teflon screw cap, a fructose syrup (150 mmol, 25% water) was placed, together with the solid acid catalyst Amberlyst-15 (300 mg), followed by adding the EG-based solvent triethylene glycol dimethyl ether (3 mL). The resulting solution was heated at 120° C. for 2 hrs while stirring at 700 rpm. After completion of the reaction, the reaction mixture was cooled to room temperature and diluted 100-fold in distilled water. HPLC analysis was conducted, indicating the production of HMF at a yield of 66%.

Example 5

In a 38 mL thick-glass-walled pressure tubular reactor (having an O.D. of 25.5 mm and a length of 20.3 cm) equipped with a Teflon screw cap, a fructose syrup (150 mmol, 25% water) was placed, together with the solid acid catalyst Amberlyst-15 (300 mg), followed by adding the EG-based solvent tetraethylene glycol dimethyl ether (3 mL). The resulting solution was heated at 120° C. for 2 hrs while stirring at 700 rpm. After completion of the reaction, the reaction mixture was cooled to room temperature and diluted 100-fold in distilled water. HPLC analysis was conducted, indicating the production of HMF at a yield of 76%.

Example 6

In a 38 mL thick-glass-walled pressure tubular reactor (having an O.D. of 25.5 mm and a length of 20.3 cm) equipped with a Teflon screw cap, a fructose syrup (150 mmol, 25% water) was placed, together with sulfuric acid (15 mmol) as an inorganic acid catalyst, followed by adding a mixture of the EG-based solvent monoethylene glycol dimethyl ether (2.7 mL) and water (0.3 mL). The resulting solution was heated at 120° C. for 3 hrs while stirring at 700 rpm. After completion of the reaction, the reaction mixture was cooled to room temperature and diluted 100-fold in distilled water. HPLC analysis was conducted, indicating the production of HMF at a yield of 91%.

Example 7

In a 38 mL thick-glass-walled pressure tubular reactor (having an O.D. of 25.5 mm and a length of 20.3 cm) equipped with a Teflon screw cap, a fructose syrup (150 mmol, 25% water) was placed, together with $NaHSO_3$ (15 mmol) as an inorganic acid catalyst, followed by adding a mixture of the EG-based solvent monoethylene glycol dimethyl ether (2.7 mL) and water (0.3 mL). The resulting solution was heated at 120° C. for 3 hrs while stirring at 700 rpm. After completion of the reaction, the reaction mixture was cooled to room temperature and diluted 100-fold in distilled water. HPLC analysis was conducted, indicating the production of HMF at a yield of 85%.

Example 8

In a 38 mL thick-glass-walled pressure tubular reactor (having an O.D. of 25.5 mm and a length of 20.3 cm) equipped with a Teflon screw cap, a fructose syrup (150 mmol, 25% water) was placed, together with p-toluenesulfonic acid (15 mmol) as an organic acid catalyst, followed by adding a mixture of the EG-based solvent monoethylene glycol dimethyl ether (2.7 mL) and water (0.3 mL). The resulting solution was heated at 120° C. for 3 hrs while stirring at 700 rpm. After completion of the reaction, the reaction mixture was cooled to room temperature and diluted 100-fold in distilled water. HPLC analysis was conducted, indicating the production of HMF at a yield of 94%.

Example 9

A solid acid catalyst was prepared by introducing sulfonic acid into amorphous carbon.

Briefly, 100 g of [EMIM]Cl was added to 10 g of wood in a 500 ml round-bottom flask. The mixture was heated at 120° C. while stirring at 650 rpm. The homogenized mixture was cooled to 10° C., followed by precipitation with ethanol. The precipitate was filtered, washed with water, and dried in vacuo. Subsequently, it was heated at 500° C. for 1 hr in a nitrogen atmosphere to give an amorphous carbon material.

The amorphous carbon material was treated with conc. $H_2SO_4$ (10%, wt/vol) while stirring at 80° C. for 2 hrs. Then, cooling, filtering, and washing with hot water were conducted, followed by additional washing with 1,4-dioxane in a Soxhlet extractor. Drying in a vacuum condition afforded a sulfonic acid-introduced carbon material.

In a 38 mL thick-glass-walled pressure tubular reactor (having an O.D. of 25.5 mm and a length of 20.3 cm) equipped with a Teflon screw cap, a fructose syrup (150 mmol, 25% water) was placed, together with the biomass-derived amorphous carbon material having sulfonic acid introduced thereinto (18 mmol) as a solid acid catalyst, followed by adding the EG-based solvent monoethylene glycol dimethyl ether (3 mL). The resulting solution was heated at 120° C. for 4 hrs while stirring at 700 rpm. After completion of the reaction, the reaction mixture was cooled to room temperature and diluted 100-fold in distilled water. HPLC analysis was conducted, indicating the production of HMF at a yield of 64%.

Example 10

In a 38 mL thick-glass-walled pressure tubular reactor (having an O.D. of 25.5 mm and a length of 20.3 cm) equipped with a Teflon screw cap, a fructose syrup (150 mmol, 25% water) was placed, together with Zeolite Y (300 mg), followed by adding the EG-based solvent monoethylene glycol dimethyl ether (3 mL). The resulting solution was heated at 120° C. for 3 hrs while stirring at 700 rpm. After completion of the reaction, the reaction mixture was cooled to room temperature and diluted 100-fold in distilled water. HPLC analysis was conducted, indicating the production of HMF at a yield of 45%.

Example 11

HMF was prepared as in Example 1, and the reaction mixture was cooled to room temperature and filtered. The filtrate was washed and dried in vacuo to recover the catalyst Amberlyst-15 while monoethylene glycol dimethyl ether was separated and recycled through distillation.

HMF was prepared in the same manner as in Example 1, with the exception that the recovered Amberlyst-15 and monoethylene glycol dimethyl ether were used. After completion of the reaction, the reaction mixture was diluted 100-fold in distilled water. HPLC analysis was conducted, indicating the production of HMF at a yield of 80%.

Comparative Example 1

In a 38 mL thick-glass-walled pressure tubular reactor (having an O.D. of 25.5 mm and a length of 20.3 cm) equipped with a Teflon screw cap, a fructose syrup (150 mmol, 25% water) was placed, together with Amberlyst-15 (300 mg) as a solid acid catalyst, followed by adding 1,3-dioxane (3 mL), which is similar in chemical structure to an EG-based solvent. The resulting solution was heated at 120° C. for 2 hrs while stirring at 700 rpm. After completion of the reaction, the reaction mixture was cooled to room temperature and diluted 100-fold in distilled water. HPLC analysis was conducted, indicating that almost no HMF was produced and that 1,3-dioxane was decomposed in an acidic condition.

Comparative Example 2

In a 38 mL thick-glass-walled pressure tubular reactor (having an O.D. of 25.5 mm and a length of 20.3 cm) equipped with a Teflon screw cap, a fructose syrup (150 mmol, 25% water) was placed, together with the solid acid catalyst Amberlyst-15 (300 mg), followed by adding tetrahydropyran (3 mL), which is similar in chemical structure to an EG-based solvent. The resulting solution was heated at 120° C. for 2 hrs while stirring at 700 rpm. After completion of the reaction, the reaction mixture was cooled to room temperature and diluted 100-fold in distilled water. HPLC analysis was conducted, indicating the production of HMF at a yield of 3%.

HMF preparation conditions and yields of Examples 1 to 11 and Comparative Examples 1 and 2 are summarized in Table 1, below.

TABLE 1

| Ex. | Solvent | Catalyst | Rxn. Temp (° C.) | HMF Yield (%) |
| --- | --- | --- | --- | --- |
| Ex. 1 | monoethylene glycol dimethyl ether | Amberlyst-15 | 120 | 80 |
| Ex. 2 | 1,4-dioxane | Amberlyst-15 | 120 | 78 |
| Ex. 3 | diethylene glycol dimethyl ether | Amberlyst-15 | 120 | 79 |
| Ex. 4 | triethylene glycol dimethyl ether | Amberlyst-15 | 120 | 66 |
| Ex. 5 | tetraethylene glycol dimethyl ether | Amberlyst-15 | 120 | 76 |
| Ex. 6 | monoethylene glycol dimethyl ether | Sulfuric acid | 120 | 91 |
| Ex. 7 | monoethylene glycol dimethyl ether | $NaHSO_3$ | 120 | 85 |
| Ex. 8 | monoethylene glycol dimethyl ether | p-toluenesulfonic acid | 120 | 94 |
| Ex. 9 | monoethylene glycol dimethyl ether | Sulfone-introduced amorphous carbon | 120 | 64 |
| Ex. 10 | monoethylene glycol dimethyl ether | Zeolite Y | 120 | 45 |
| Ex. 11 | monoethylene glycol dimethyl ether | Amberlyst-15 | 120 | 80 |
| C. Ex. 1 | 1,3-dioxane | Amberlyst-15 | 120 | 0 |
| C. Ex. 2 | tetrahydropyran | Amberlyst-15 | 120 | 3 |

As is understood from the data of Table 1, 5-hydroxymethyl-2-furfural was prepared at a far higher yield in the manner described in one of Examples 1 to 11, compared to Comparative Examples 1 and 2, in which no biomass-derived, ethylene glycol-based solvents were employed.

Test Example 1: HPLC (High Performance Liquid Chromatography) Analysis

Figure 3:
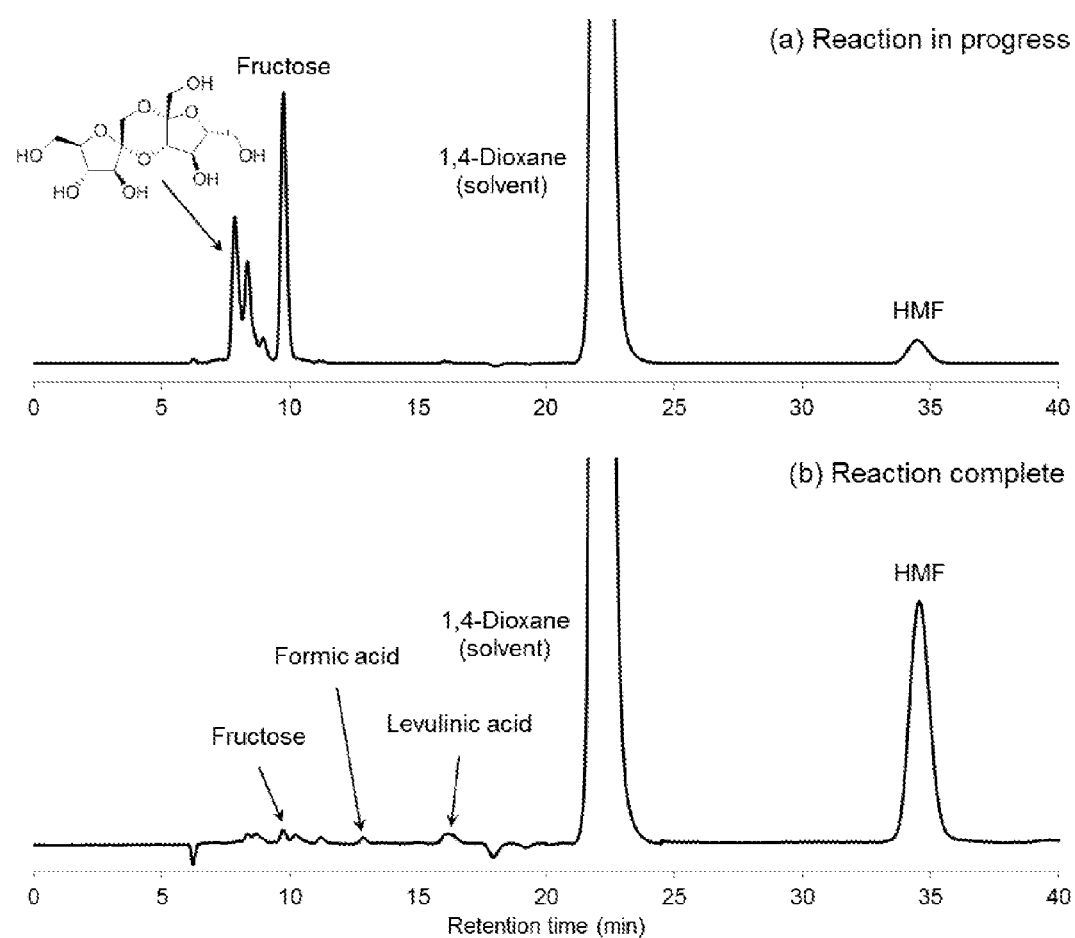
FIG. 3 shows the change in the HPLC chromatogram during the preparation of 5-hydroxymethyl-2-furfural as measured in Test Example 1.

HPLC chromatograms were read during the reaction (a) and at the time of completion of the reaction (b) in Example 2, as shown in FIG. 3.

As can be seen in FIG. 3, when the biomass-derived, ethylene glycol-based compound 1,4-dioxane was employed, many intermediates were generated and then disappeared. As elucidated in conjunction with the dehydration mechanism above, the intermediates serve to block the progression of a pathway directing the conversion of fructose into by-products.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. A method for preparing 5-hydroxymethyl-2-furfural, comprising converting fructose into 5-hydroxymethyl-2-furfural in presence of an acid catalyst in a linear ethylene glycol-based compound as a solvent, wherein the acid catalyst is a solid acid catalyst and is structured to have an organic or inorganic support to which a Bronsted acid or a Lewis acid is linked as a functional group, wherein the linear ethylene glycol-based compound is represented by the following Structural Formula 1:

[Structural Formula 1]

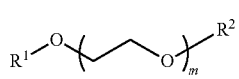

wherein, $R^1$ and $R^2$ may be the same or different and are each independently C1 to C6 alkyl, and m is an integer of 1 to 6.

2. The method of claim 1, wherein $R^1$ and $R^2$ may be the same or different and are each independently methyl or ethyl, and m is an integer of 1 to 4.

3. The method of claim 1, wherein the linear ethylene glycol-based compound is derived from ethanol, the ethanol being prepared from biomass by fermentation.

4. The method of claim 1, wherein the linear ethylene glycol-based compound is selected from a group consisting of monoethylene glycol dimethyl ether, diethylene glycol dimethyl ether, triethylene glycol dimethyl ether, tetraethylene glycol dimethyl ether, and a combination thereof.

5. The method of claim 1, wherein the fructose is provided as a fructose syrup having a water content of 10 to 50 weight parts per 100 weight parts of fructose.

6. The method of claim 1, wherein the organic support is at least one selected from the group consisting of polystyrene, polyamide, and polyethylene glycol.

7. The method of claim 1, wherein the inorganic support comprises at least one selected from among silica, alumina, and zeolite.

8. The method of claim 1, wherein the solid acid catalyst has amorphous carbon into which a sulfonic acid group is introduced, the amorphous carbon being formed by incompletely carbonizing biomass.

9. The method of claim 1, wherein the converting is carried out at 80 to 150° C.

10. The method of claim 1, further comprising recovering the solid acid catalyst from the solvent after the converting.

* * * * *